United States Patent
Govari et al.

(10) Patent No.: US 9,005,193 B2
(45) Date of Patent: Apr. 14, 2015

(54) MULTICHANNEL ABLATION WITH FREQUENCY DIFFERENTIATION

(75) Inventors: Assaf Govari, Haifa (IL); Andres Claudio Altmann, Haifa (IL); Yaron Ephrath, Karkur (IL)

(73) Assignee: Biosense Webster (Israel) Ltd. (IL)

( * ) Notice: Subject to any disclaimer, the term of this patent is extended or adjusted under 35 U.S.C. 154(b) by 1179 days.

(21) Appl. No.: 12/951,200

(22) Filed: Nov. 22, 2010

(65) Prior Publication Data

US 2012/0116387 A1 May 10, 2012

Related U.S. Application Data

(63) Continuation-in-part of application No. 12/941,165, filed on Nov. 8, 2010.

(51) Int. Cl.
*A61B 18/04* (2006.01)
*A61B 18/12* (2006.01)
*A61B 18/00* (2006.01)

(52) U.S. Cl.
CPC ... *A61B 18/1206* (2013.01); *A61B 2018/00779* (2013.01); *A61B 2018/00875* (2013.01); *A61B 2018/124* (2013.01); *A61B 2018/128* (2013.01)

(58) Field of Classification Search
USPC .............................. 606/34, 37, 41
See application file for complete search history.

(56) References Cited

U.S. PATENT DOCUMENTS

| | | | |
|---|---|---|---|
| 5,542,916 A * | 8/1996 | Hirsch et al. ............... 604/22 |
| 5,782,828 A | 7/1998 | Chen et al. |
| 5,931,835 A | 8/1999 | Mackey |
| 5,954,686 A | 9/1999 | Garito |
| 6,027,500 A | 2/2000 | Buckles et al. |
| 6,254,600 B1 | 7/2001 | Willink |
| 6,582,427 B1 * | 6/2003 | Goble et al. ............... 606/37 |
| 6,730,078 B2 * | 5/2004 | Simpson et al. ............ 606/34 |
| 7,468,062 B2 | 12/2008 | Oral et al. |
| 7,691,097 B2 * | 4/2010 | Miyazawa ................. 606/1 |
| 2002/0022836 A1 * | 2/2002 | Goble et al. ............... 606/34 |
| 2003/0130711 A1 | 7/2003 | Pearson et al. |
| 2003/0153908 A1 * | 8/2003 | Goble et al. ............... 606/41 |
| 2003/0163123 A1 * | 8/2003 | Goble et al. ............... 606/34 |
| 2003/0163124 A1 * | 8/2003 | Goble ....................... 606/37 |
| 2003/0199862 A1 * | 10/2003 | Simpson et al. ............ 606/34 |
| 2005/0245922 A1 * | 11/2005 | Goble ....................... 606/37 |
| 2006/0030845 A1 * | 2/2006 | Leung et al. ............... 606/41 |
| 2006/0155270 A1 | 7/2006 | Hancock |

(Continued)

FOREIGN PATENT DOCUMENTS

EP          1334699 A1     8/2003

OTHER PUBLICATIONS

European Search Report, for EPA Appln. No. 13159798.1-1652, dated Jun. 11, 2013.

(Continued)

*Primary Examiner* — Joseph Stoklosa
*Assistant Examiner* — Jocelyn D Ram

(57) ABSTRACT

Apparatus, including an energy generator, configured to supply first ablation power modulated at a first frequency and second ablation power modulated at a second frequency different from the first frequency. The apparatus also includes a probe, having at least one electrode coupled to receive the first and second ablation powers simultaneously and to dissipate the first and second ablation powers in body tissue in contact with the at least one electrode.

24 Claims, 3 Drawing Sheets

(56) References Cited

U.S. PATENT DOCUMENTS

| | | |
|---|---|---|
| 2007/0129716 A1 | 6/2007 | Daw |
| 2007/0191827 A1 | 8/2007 | Lischinsky |
| 2007/0225699 A1* | 9/2007 | Goble et al. .................. 606/34 |
| 2008/0058635 A1 | 3/2008 | Halperin et al. |
| 2008/0294156 A1* | 11/2008 | Newton et al. ................ 606/34 |
| 2009/0062786 A1* | 3/2009 | Garito et al. ................. 606/37 |
| 2010/0145329 A1 | 6/2010 | Bystryak |
| 2012/0116387 A1* | 5/2012 | Govari et al. ................. 606/41 |

OTHER PUBLICATIONS

U.S. Appl. No. 12/941,165—pending.
EP Search Report Appln No. 11 18 8103 dated Feb. 24, 2012.
EP Search Report Appln No. 11 18 8096 dated Feb. 28, 2012.

* cited by examiner

MULTICHANNEL ABLATION WITH FREQUENCY DIFFERENTIATION

CROSS-REFERENCE TO RELATED APPLICATION

This application is a continuation-in-part of U.S. patent application Ser. No. 12/941,165, filed 8 Nov. 2010, which is incorporated herein by reference.

FIELD OF THE INVENTION

The present invention relates generally to invasive medical devices, and specifically to radio-frequency ablation of tissue using differing frequencies.

BACKGROUND OF THE INVENTION

Ablation of body tissue, using multiple electrodes, is known in the art. The ablation is typically performed by applying alternating currents to the electrodes, at a sufficient power to cause the ablation. Typically, the electrodes are mounted on a distal tip of a catheter which is inserted into a lumen of a subject.

The distal tip may be tracked in a number of different ways known in the art, for example by measuring magnetic fields, generated by coils external to the subject, at the distal tip.

U.S. Pat. No. 5,931,835 to Mackey, whose disclosure is incorporated herein by reference, describes a radio frequency energy delivery system for multipolar electrode catheters. The disclosure states that the electrodes may be simultaneously energized in phase with each other to achieve a desired lesion pattern.

U.S. Pat. No. 5,782,828 to Chen, et al., whose disclosure is incorporated herein by reference, describes an ablation catheter having multiple electrodes and a close-loop control mechanism for each electrode with a temperature sensor.

U.S. Pat. No. 7,468,062 to Oral, et al., whose disclosure is incorporated herein by reference, describes an atrial ablation catheter with an electrode array.

U.S. Pat. No. 6,027,500 to Buckles, et al., whose disclosure is incorporated herein by reference, describes a catheter with a plurality of electrodes disposed adjacent to a distal end of the probe. One of the electrodes is an ablation electrode.

U.S. Patent Application 2003/0130711 to Pearson, et al., whose disclosure is incorporated herein by reference, describes apparatus for carrying out thermal ablation of target tissue. The apparatus includes a radio-frequency ablation device having a multi-electrode electrode assembly.

U.S. Patent Application 2008/0058635 to Halperin, et al., whose disclosure is incorporated herein by reference, describes a magnetic resonance imaging system including an invasive combined electrophysiology and imaging antenna catheter having diagnostic electrodes for receiving electrical potentials.

The description above is presented as a general overview of related art in this field and should not be construed as an admission that any of the information it contains constitutes prior art against the present patent application.

SUMMARY OF THE INVENTION

An embodiment of the present invention provides apparatus, including:

an energy generator, configured to supply first ablation power modulated at a first frequency and second ablation power modulated at a second frequency different from the first frequency; and a probe, having at least one electrode coupled to receive the first and second ablation powers simultaneously and to dissipate the first and second ablation powers in body tissue in contact with the at least one electrode.

Typically the energy generator includes:

a power source configured to supply the first and second ablation powers at a base radio frequency; and first and second modulators, which are coupled to receive and to modulate the first and second ablation powers at the first and second frequencies, respectively.

The at least one electrode may have a first electrode configured to receive the first ablation power, and a second electrode configured to receive the second ablation power. The apparatus may further include: a first power measuring unit coupled to the first electrode and configured to determine a first value of the first ablation power; and a second power measuring unit coupled to the second electrode and configured to determine a second value of the second ablation power.

The first power measuring unit typically includes first and second demodulators coupled to respectively receive signals at the base radio frequency and at the first frequency, and the second power measuring unit may include third and fourth demodulators coupled to respectively receive signals at the base radio frequency and at the second frequency.

In a disclosed embodiment the modulation consists of phase modulation.

In an alternative embodiment the at least one electrode includes a single electrode configured as a source electrode for the first ablation power and as a return electrode for the second ablation power.

In a further alternative embodiment the at least one electrode includes a first electrode configured as a source electrode for the first ablation power and a second electrode configured as a return electrode for the first ablation power.

In a yet further disclosed embodiment the at least one electrode includes a first electrode configured as a source electrode for the first ablation power and a second electrode configured as a source electrode for the second ablation power. The apparatus may include a further electrode coupled to the body tissue and configured to act as a return electrode for the first and second ablation powers.

The apparatus may include a controller which is configured to receive an indication of a value of at least one of the first and second ablation powers dissipated in the body tissue, and to determine an impedance of the body tissue in response to the value. Typically, the controller is configured to assess a degree of ablation of the body tissue in response to the impedance. The energy generator may be configured to adjust a level of at least one of the first ablation power and the second ablation power in response to the impedance.

In one embodiment at least one of the first ablation power and the second ablation power are supplied simultaneously in a unipolar mode and a bipolar mode.

There is further provided, according to an embodiment of the present invention, a method, including:

generating first ablation power modulated at a first frequency;

generating second ablation power modulated at a second frequency different from the first frequency; and coupling at least one electrode of a probe to receive the first and second ablation powers simultaneously and to dissipate the first and second ablation powers in body tissue in contact with the at least one electrode.

The method typically includes:

supplying the first and second ablation powers at a base radio frequency; and receiving and modulating the first and second ablation powers at the first and second frequencies respectively.

The present invention will be more fully understood from the following detailed description of the embodiments thereof, taken together with the drawings in which:

DETAILED DESCRIPTION OF EMBODIMENTS

Overview

Figure 1:
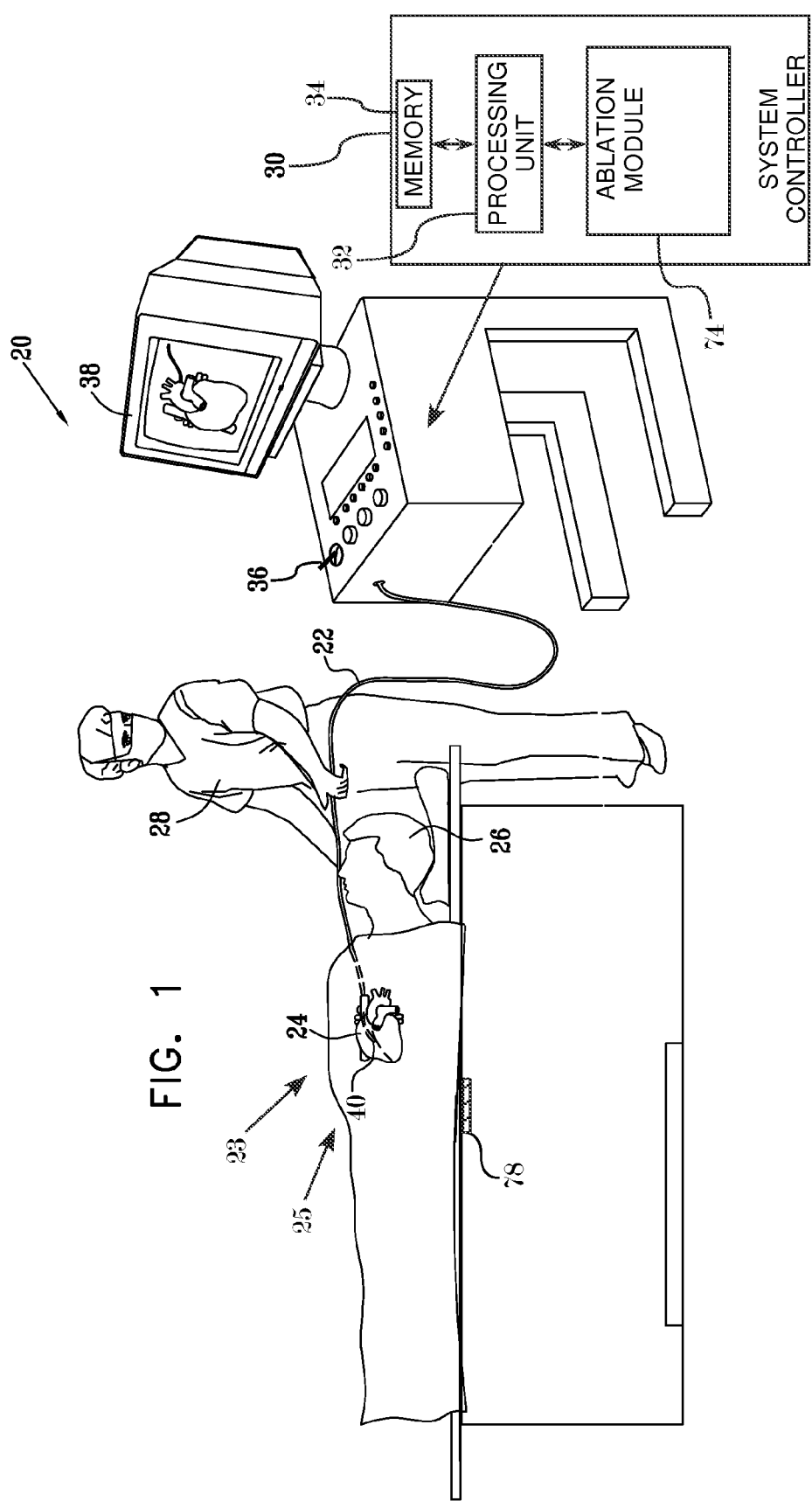
FIG. 1 is a schematic, pictorial illustration of a catheter ablating system, according to an embodiment of the present invention.

An embodiment of the present invention provides an improved system for ablating tissue using one or more electrodes attached to a probe. The electrodes are typically attached to the distal tip of a catheter probe. Typically there are a plurality of electrodes, and each electrode may be configured to supply ablation power. Typically, the power is provided to the electrodes in the form of a base radio frequency which is modulated. Different modulation frequencies may be used for different electrodes.

An ablation module, typically incorporated as part of a catheter ablating system, acts as an ablation energy generator for the system. The module comprises a frequency generator which generates the base frequency as well as the modulating frequencies used to modulate the base frequency. The module also typically includes a respective power amplifier for each electrode of the probe. Modulated base frequency signals are input to the power amplifiers, which output amplified modulated power signals to their respective electrodes. The module may be configured to operate in a unipolar mode or in a bipolar mode.

For operation in a unipolar mode, the module is configured so that each of the probe electrodes acts as a source electrode. An electrode connected to a subject whose tissue is being ablated is used as a common return electrode. The return electrode is typically placed in contact with the skin of the subject.

For operation in a bipolar mode, the module may be configured so that for a pair of electrodes on the probe one is a source electrode and the other is a return electrode, for a given modulated frequency power. Typically, more than one pair of electrodes may be configured in this manner.

In an alternative bipolar mode of operation, any specific electrode may be configured as a source electrode for a first modulated frequency, and as a return electrode for a different second modulated frequency. To explain this arrangement, assume that another electrode acts as a source electrode for the second modulated frequency signal. The specific electrode considered here may be configured as a return electrode for the second modulated frequency signal, by applying a phase inversion to this frequency. The first modulated frequency signal and the inverted second modulated frequency signal are summed in an adder, and the summed signal output by the adder is used as an input to the power amplifier of the specific electrode.

By applying differently modulated signals to the electrodes, a controller of the ablation system is able to monitor the power dissipated by each modulated signal separately. If necessary, the controller may then individually adjust the power dissipated at each electrode, by varying a level of the modulated power input to a power amplifier supplying the electrode, and/or by varying a gain of the power amplifier. Since ablated tissue typically has a different impedance from non-ablated tissue, and since the tissue impedance affects the power dissipated, monitoring of the separate powers dissipated allows the controller to estimate and adjust the degree of ablation of the tissue from each electrode.

DETAILED DESCRIPTION

Figure 2:
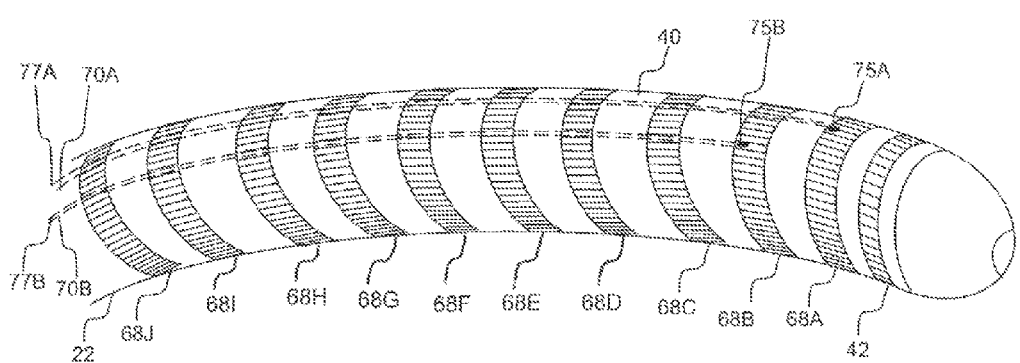
FIG. 2 is a schematic diagram of a distal tip of a catheter used in the system of FIG. 1, according to an embodiment of the present invention.

Reference is now made to FIG. 1, which is a schematic, pictorial illustration of a catheter ablating system 20, and to FIG. 2 which is a schematic diagram of a distal tip of a catheter probe 22 used in the system, according to embodiments of the present invention. In system 20, probe 22 is inserted into a lumen 23, such as a chamber of a heart 24, of a subject 26. Typically, the probe is used by a medical practitioner 28 during a procedure which includes performing ablation of tissue 25. However, the probe may be configured to perform functions in addition to ablation, such as measuring potentials of heart tissue. The functioning of system 20 is managed by a system controller (SC) 30, comprising a processing unit 32 communicating with a memory 34, wherein is stored software for operation of system 20. Controller 30 is typically an industry-standard personal computer (PC) comprising a general-purpose computer processor. However, in some embodiments, at least some of the functions of the controller are performed using custom-designed hardware and software, such as an application specific integrated circuit (ASIC) or a field programmable gate array (FPGA). Controller 30 is typically operated by practitioner 28 using a pointing device 36 and graphic user interface (GUI) 38, which enable the practitioner to set parameters of system 20. GUI 38 typically also displays results of the procedure to the medical practitioner.

The software in memory 34 may be downloaded to the controller in electronic form, over a network, for example. Alternatively or additionally, the software may be provided on non-transitory tangible media, such as optical, magnetic, or electronic storage media.

A distal tip 40 of probe 22 comprises at least one electrode 42 which, in a disclosed embodiment, is used in tracking the position of the distal tip, by methods which are known in the art. However, electrode 42 may be used for other purposes, as well, such as for electrophysiological sensing. The electrode is connected by a wire (not shown) in probe 22 to driver and measurement circuitry in system controller 30. Using position coordinates determined by the tracking, the system controller is able to show the position of the distal tip inside the heart on GUI 38.

Alternatively or additionally, the distal tip may be tracked by other systems known in the art, for example, by a magnetic tracking system. One such magnetic tracking system is the CARTO 3 system, produced by Biosense Webster, Inc, Diamond Bar, Calif., which tracks the distal tip by using alternating magnetic fields to induce corresponding positioning currents in coils in the tip. The fields are typically set to alternate at frequencies of 1-3 kHz, but may be set to alternate at higher frequencies, up to 50 kHz or more. The frequencies of the magnetic fields are herein termed magnetic positioning frequencies, $f_{magnetic\_posit}$.

Distal tip 40 also comprises a multiplicity of ablation electrodes that are typically located on the outer surface of the distal tip. By way of example, tip 40 is herein assumed to comprise 10 electrodes 68A, 68B, 68C, 68D, 68E, 68F, 68G, 68H, 68I and 68J, but it will be understood that embodiments of the present invention may use any convenient plurality of ablation electrodes. The multiplicity of ablation electrodes are also herein collectively termed ablation electrodes 68 is separately connected by a respective conducting wire 70A, 70B, 70C, 70D, 70E, 70F, 70G, 70H, 70I, 70J to an ablation module 74 in controller 30. (For simplicity, only wires 70A, 70B are shown in FIG. 2.) Module 74 is described in more detail below, with reference to FIG. 3, and may be configured to provide ablation current in a unipolar or a bipolar mode.

In the unipolar mode, the ablation current transfers from an ablation electrode 68, acting as a source electrode, to the tissue being ablated and the current path is completed via a return electrode 78 (FIG. 1), external to lumen 23. Return electrode 78 is typically placed in contact with the skin, for example the back, of subject 26, and acts as a local ground electrode.

In the bipolar mode, the ablation current transfers between pairs of ablation electrodes 68 via the tissue being ablated. Each electrode 68 may be configured as either a source electrode or as a return electrode. For example, the ten electrodes may be arranged as five pairs 68A-68B, 68C-68D, 68E-68F, 68G-68H, and 68I-68J. Alternatively, at least some electrodes 68 may act as both a source electrode and as a return electrode. For example, the ten electrodes may be arranged as nine pairs 68A-68B, 68B-68C, 68C-68D, 68D-68E, 68E-68F, 68F-68G, 68G-68H, 68H-68I, and 68I-68J. In this arrangement, electrodes 68B, 68C, 68D, 68E, 68F, 68G, 68H, 68I are both source electrodes and return electrodes, electrode 68A is only a source electrode, and electrode 68J is only a return electrode.

Figure 3:
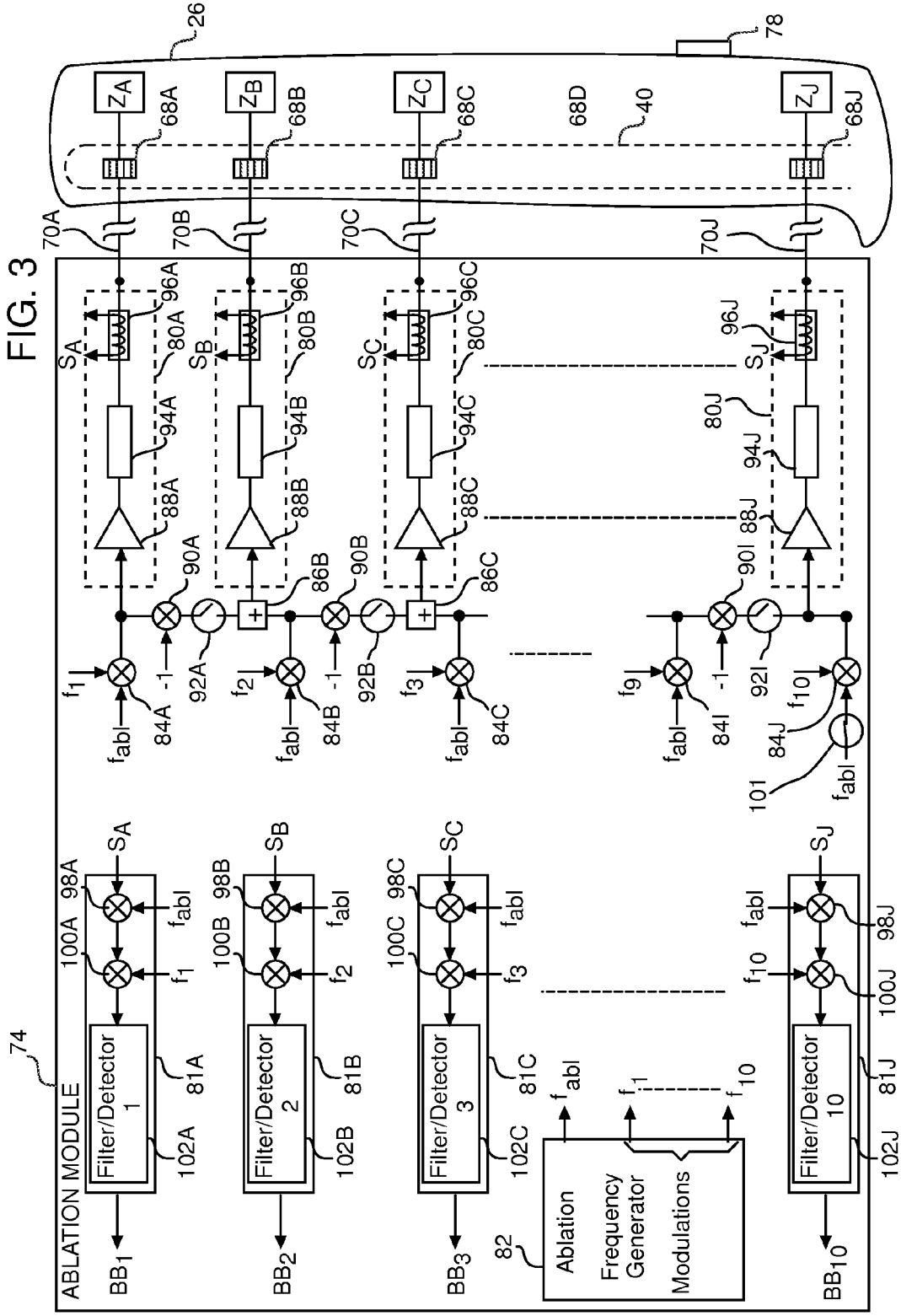
FIG. 3 is a schematic circuit diagram of an ablation module, according to an embodiment of the present invention.

FIG. 3 is a schematic circuit diagram of module 74, according to an embodiment of the present invention. FIG. 3 also schematically illustrates some of the elements relevant to distal tip 40, using the same identifying numerals as are used in the description of the elements above. Module 74 acts as an ablation energy generator, and is herein also referred to as generator 74. While for clarity in the description of generator 74 elements of the generator are assumed to be discrete elements, it will be appreciated that some or all of the elements may be implemented in combination with each other, typically as integrated circuits. It will also be appreciated that at least some of the functions of the elements, for example a phase inversion referred to below, may be implemented in software.

Generator 74 comprises a respective current supply source 80A, . . . for each electrode 68, so that for the exemplary embodiment described above, there are ten current supplies 80A, . . . , 80J. The multiplicity of supplies are also herein collectively termed supplies 80.

For simplicity, only circuit diagrams for current supplies 80A, 80B, 80C, and 80J are shown in the figure.

While generator 74 has separate current supplies 80, the supplies are driven at a single ablation base radio frequency, $f_{abl}$. The currents from each supply 80 are distinguished by applying a respective unique different modulating frequency $f_1, f_2, \ldots f_{10}$ to each of the supplies 80A, 80B, . . . 80J. Distinguishing the currents in this manner virtually eliminates cross-talk between the current supplies, as well as allowing measurements such as power dissipation and impedance to be made for the individual current supplies. A frequency generator 82, under direction from controller 30, is configured to act as a power source producing a driving alternating voltage signal at the ablation frequency $f_{abl}$, as well as driving modulation voltage signals at the different modulating frequencies $f_1, f_2, \ldots f_{10}$ required by current supplies 80.

Frequency generator 82 is typically a phase-locked loop device. The ablation frequency $f_{abl}$ is typically in the range of 400-600 kHz, although other frequencies may be used. The different modulating frequencies are typically in the range of 8 kHz-80 kHz, and are typically well separated from the magnetic positioning frequencies $f_{magnetic\_posit}$. However, frequencies outside the range 8 kHz-80 kHz may be used for the modulating frequencies.

Each current supply 80A, 80B, . . . is constructed from substantially similar components, and all supplies perform substantially the same function of delivering ablation power, in the form of ablating current, to a respective electrode. For each current supply 80A, 80B, . . . generator 74 has a respective power measuring unit 81A, 81B, . . . . All adjustable elements of generator 74, such as the power measuring units, amplifiers, switches, mixers, and filtration and attenuation circuitry of the current supplies, are under overall control of controller 30.

The following description applies to current supply 80B, wherein elements of the supply have a suffix B after the identifying numeral. Except where otherwise stated, substantially the same description applies to other current supplies in generator 74, such as current supplies 80A, 80C, . . . , and 80J, and those having ordinary skill in the art will be able to adapt the description for the other current supplies, mutatis mutandis, for example by altering the suffix of the identifying numeral and/or the subscript of the identifying letter. By way of example, first demodulator 98A, 98B, 98C, . . . , 98J are all functionally equivalent; second demodulators 100A, 100B, 100C, . . . , 100J are all functionally equivalent; modulators 84A, 84B, 84C, . . . , 84J are all functionally equivalent; adder 86A, 86B, 86C, . . . , 86J are all functionally equivalent; amplifier 88A, 88B, 88C, . . . , 88J are all functionally equivalent; inverter 90A, 90B, 90C, . . . , 90J are all functionally equivalent; switch 92A, 92B, 92C, . . . , 92I, are all functionally equivalent; circuitry 94A, 94B, 94C, . . . , 94J are all functionally equivalent; sensing element 96A, 96B, 96C, . . . , 96J are all functionally equivalent; wire 70A, 70B, 70C, . . . , 70J are all functionally equivalent; power measuring unit 81A, 81B, 81C, . . . , 81J are all functionally equivalent; and filter/detector circuitry 102A, 102B, 102C, . . . , 102J are all functionally equivalent.

The modulated input for current supply 80B is derived from a mixer 84B, also referred to herein as modulator 84B, which receives as inputs ablation frequency $f_{abl}$ and modulating frequency $f_2$ from generator 82. The mixer outputs a low level modulated ablation power signal, typically a phase modulated low level power signal, having frequency components derived from $f_{abl}$ and $f_2$.

(For current supply 80J a controlling switch 101 controls whether a mixer 84J receives ablation frequency $f_{abl}$, and thus whether the mixer outputs $f_{10}$-modulated power. The function of switch 101 is explained below.)

The low level modulated output from modulator 84B is transferred via an adder 86B to a power amplifier 88B. Amplifier 88B may also receive, via adder 86B, a low level modulated output from a mixer 84A which has been inverted in phase by a phase inverter 90A. The inverted modulated output from inverter 90A has substantially the same amplitude and frequency as the output from mixer 84A, but differs in phase by 180°. Adder 86B receives the inverted output from inverter 90A if a switch 92A is closed, and sums the inverted output with the output from modulator 84B to provide a low level input for amplifier 88B. If the switch is not closed adder 86B only receives the modulated output from mixer 84B, and provides this as the amplifier's low level input.

Amplifier 88B amplifies its low level input, generating high level ablation power at a value that is controlled by controller 30, since the controller typically controls the gain of the amplifier. Typically the power generated is in the range of approximately 10 W-approximately 100 W, although the amplifier may be configured to generate power outside this range.

The high level output from amplifier 88B may be transferred through circuitry 94B, via wire 70B, to electrode 68B. Circuitry 94B typically comprises filtering and/or attenuating elements, such as those described in U.S. patent application Ser. No. 12/941,165.

Typically, a sensing element 96B is placed in series with wire 70B, to enable controller 30 to determine, inter alia, a power input to electrode 68B. Element 96B typically comprises a current sensing transformer, which generates a signal $S_B$ directly proportional to the current in wire 70B. A suitable current sensing transformer is a CST device produced by Coilcraft, of Cary Ill. Alternatively, other methods for determining the power input to the electrode, such as by the controller measuring voltages at the output of amplifier 88B, may be used. Signal $S_B$ is input to power measuring unit 81B.

Power measuring unit 81B comprises a first demodulator 98B, which is connected to receive signal $S_B$ from element 96B, and ablation frequency $f_{abl}$ from generator 82. Demodulator 98B is configured to act as a homodyne demodulator, essentially removing ablation frequency components from signal $S_B$, while outputting modulation frequency components having frequencies $f_1, f_2, \ldots$.

A second demodulator 100B in unit 81B receives the modulation frequency components output by demodulator 98B. The second demodulator is typically also connected to receive modulation frequency $f_2$ from generator 82, and is also configured as a homodyne demodulator. The output from the second demodulator is filtered in filter/detector circuitry 102B, which filters out all modulation frequency components apart from frequency $f_2$, and which converts the frequency component $f_2$ to a baseband signal $BB_2$. Controller 30 receives signal $BB_2$, and uses it to measure the power dissipated in body 26 by the $f_2$-modulated current generated by source 80B.

Alternatively or additionally, second demodulator 100B may be configured to receive modulation frequency $f_1$ from generator 82, and to act as a homodyne demodulator for this frequency. Such a configuration is appropriate if electrode 68B acts as a return electrode for $f_1$-modulated power when switch 92A is closed, as is explained below. In this case signal $BB_2$ is a measure of the $f_1$-modulated current received by electrode 68B.

From the above description it will be apparent that second demodulator 100B may be configured to measure $f_1$-modulated current or $f_2$-modulated current, or both types of current. The latter configuration may be implemented, for example, by switching the demodulator between receiving frequency $f_1$ and frequency $f_2$. Alternatively, the demodulation at the two frequencies may be performed by sampling the signal and correlating the samples with the $f_1$ and $f_2$ frequencies.

FIG. 3 shows, by way of example, switches 92A, 92B, ..., 92I open, and switch 101 closed. Assuming that electrode 78 is configured as a return electrode, the exemplary configuration illustrated in the figure shows generator 74 operating in a solely unipolar mode, where all electrodes 68 of probe 40 act only as source electrodes. Other configurations of switches 92A, ... 92I, and 101 cause at least some electrodes 68 to act as both a source electrode and a return electrode, or just as a return electrode, or just as a source electrode.

For example, if switches 92A, 92B, ..., 92I are closed, and switch 101 is open, electrode 68A acts only as a source electrode of $f_1$-modulated power, electrode 68B acts as a return electrode of the $f_1$-modulated power and as a source electrode of $f_2$-modulated power, and electrode 68J acts only as a return electrode of $f_9$-modulated power. In this configuration electrodes 68C, ... 68I act similarly to electrode 68B, i.e., as both source and return electrodes, and generator 74 operates in a solely bipolar mode.

Other arrangements of switches 92A, 92B, ..., 92I, switch 101, as well as of other switches which for simplicity are not shown in the figure but which will be apparent to those having ordinary skill in the art, cause generator 74 to operate in different solely bipolar modes. For example, various switches may be opened or closed to allow bipolar current transfer to occur between pairs of electrodes (68A, 68B), (68C, 68D), (68E, 68F), (68G, 68H), and (68I, 68J), where the first electrode in a pair acts only as a source electrode and the second electrode in the pair acts only as a return electrode.

Arrangements of the switches of generator 74, causing the generator to operate in a mixed simultaneous unipolar/bipolar mode, will be apparent to those having ordinary skill in the art.

For example, electrode 68A may be configured as a source for $f_1$-modulated power, and electrode 68B as a return for the $f_1$-modulated power. Electrodes 68C, ..., 68J may be configured as respective source electrodes for $f_3, \ldots f_{10}$ modulated powers, with electrode 78 acting as the return electrode. In this case bipolar current transfer occurs between electrode pair (68A, 68B), and simultaneously unipolar current transfer occurs from electrodes 68A, 68C, ... 68J. Thus, electrodes 68C, ... 68J are only operative in a unipolar mode, electrode 68B is only operative in a bipolar mode, and electrode 68A is operative in both a unipolar and a bipolar mode.

Generator 74 enables controller 30 to operate system in a variety of modes, as exemplified above. In each of these modes, different frequencies of modulation applied to the base ablation radio frequency allow the controller to monitor separately and distinctly values of the power dissipated by, and/or the impedance presented to, each electrode 68 at each different modulated frequency regardless of whether the electrodes are operative in a solely unipolar mode, in a solely bipolar mode, or in a mixed unipolar/bipolar mode. Furthermore, as explained above, the controller may also adjust the frequency-modulated power dissipated by each electrode. Thus, since the impedance of tissue varies according to the degree of ablation of the tissue, monitoring the impedance presented to individual electrodes allows the controller to assess, validate, and adjust the ablation performed by the individual electrodes.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
   a controller;
   an energy generator operatively connected to the controller, the energy generator configured to supply first ablation power modulated at a first frequency and second ablation power modulated at a second frequency different from the first frequency, wherein the energy generator comprising a power source configured to supply the first and second ablation powers at a base radio frequency; first and second modulators, which are coupled to receive and to modulate the first and second ablation powers at the first and second frequencies, respectively; and a first power measuring unit having a first demodulator; and a probe operatively connected to the energy generator, the probe comprising at least one electrode coupled to receive the first and second ablation powers simultaneously and to dissipate the first and second ablation powers in body tissue in contact with the at least one electrode, wherein the controller is configured to use an output from the first demodulator and the first and second modulated ablation powers to measure the power dissipated in the body tissue.

2. The apparatus according to claim 1, wherein the at least one electrode comprises a first electrode configured to receive the first ablation power, and a second electrode configured to receive the second ablation power, wherein, the first power measuring unit is coupled
to the first electrode and configured to determine a first value of the first ablation power; and
a second power measuring unit is coupled to the second electrode and configured to determine a second value of the second ablation power.

3. The apparatus according to claim 2, wherein the first power measuring unit further comprises a second demodulator, the first and second demodulators being coupled to respectively receive signals at the base radio frequency and at the first frequency, and wherein the second power measuring unit comprises third and fourth demodulators coupled to respectively receive signals at the base radio frequency and at the second frequency.

4. The apparatus according to claim 1, wherein the modulation comprises phase modulation.

5. The apparatus according to claim 1, wherein the at least one electrode comprises a single electrode configured as a source electrode for the first ablation power and as a return electrode for the second ablation power.

6. The apparatus according to claim 1, wherein the at least one electrode comprises a first electrode configured as a source electrode for the first ablation power and a second electrode configured as a return electrode for the first ablation power.

7. The apparatus according to claim 1, wherein the at least one electrode comprises a first electrode configured as a source electrode for the first ablation power and a second electrode configured as a source electrode for the second ablation power.

8. The apparatus according to claim 7, and comprising a further electrode coupled to the body tissue and configured to act as a return electrode for the first and second ablation powers.

9. The apparatus according to claim 1, wherein the controller is configured to receive an indication of a value of at least one of the first and second ablation powers dissipated in the body tissue, and to determine an impedance of the body tissue in response to the value.

10. The apparatus according to claim 9, wherein the controller is configured to assess a degree of ablation of the body tissue in response to the impedance.

11. The apparatus according to claim 9, wherein the energy generator is configured to adjust a level of at least one of the first ablation power and the second ablation power in response to the impedance.

12. The apparatus according to claim 1, wherein at least one of the first ablation power and the second ablation power is supplied simultaneously in a unipolar mode and a bipolar mode.

13. A method, comprising:
generating first ablation power modulated at a first frequency;
generating second ablation power modulated at a second frequency different from the first frequency;
supplying the first and second ablation powers at a base radio frequency;
receiving and modulating the first and second ablation powers at the first and second frequencies respectively;
coupling at least one electrode of a probe to receive the first and second ablation powers simultaneously and to dissipate the first and second ablation powers in body tissue in contact with the at least one electrode; and
measuring power dissipated into the body tissue using a first power measuring unit having a first demodulator using an output from the first demodulator and the first and second modulated ablation powers.

14. The method according to claim 13, wherein the at least one electrode comprises a first electrode configured to receive the first ablation power, and a second electrode configured to receive the second ablation power and comprising:
coupling the first power measuring unit to the first electrode so as to determine a first value of the first ablation power; and
coupling a second power measuring unit to the second electrode so as to determine a second value of the second ablation power.

15. The method according to claim 14, wherein the first power measuring unit further comprises a second demodulator, the first second demodulators being coupled to respectively receive signals at the abase radio frequency and at the first frequency and wherein the second power measuring unit comprises third and fourth demodulators coupled to respectively receive signals at the base radio frequency and at the second frequency.

16. The method according to claim 13, wherein the modulating comprises phase modulating.

17. The method according to claim 13, wherein the at least one electrode comprises a single electrode configured as a source electrode for the first ablation power and as a return electrode for the second ablation power.

18. The method according to claim 13, wherein the at least one electrode comprises a first electrode configured as a source electrode for the first ablation power and a second electrode configured as a return electrode for the first ablation power.

19. The method according to claim 13, wherein the at least one electrode comprises a first electrode configured as a source electrode for the first ablation power and a second electrode configured as a source electrode for the second ablation power.

20. The method according to claim 19, and comprising coupling a further electrode to the body tissue to act as a return electrode for the first and second ablation powers.

21. The method according to claim 13, and comprising receiving an indication of a value of at least one of the first and second ablation powers dissipated in the body tissue, and determining an impedance of the body tissue in response to the value.

22. The method according to claim 21, and comprising assessing a degree of ablation of the body tissue in response to the impedance.

23. The method according to claim 21, and comprising adjusting a level of at least one of the first ablation power and the second ablation power in response to the impedance.

24. The method according to claim 13, and comprising supplying at least one of the first ablation power and the second ablation power simultaneously in a unipolar mode and a bipolar mode.

* * * * *